United States Patent
Halseth et al.

(10) Patent No.: US 7,056,306 B1
(45) Date of Patent: Jun. 6, 2006

(54) FLUID SAMPLING DEVICE WITH RETRACTABLE NEEDLE

(75) Inventors: Thor R Halseth, Simi Valley, CA (US); John M Barker, Ventura, CA (US); Robert Hall, Thousand Oaks, CA (US); Michael J Botich, Oxnard, CA (US)

(73) Assignee: MDC Investment Holdings, Inc., Wilminton, DE (US)

( * ) Notice: Subject to any disclaimer, the term of this patent is extended or adjusted under 35 U.S.C. 154(b) by 296 days.

(21) Appl. No.: 09/633,793

(22) Filed: Aug. 7, 2000

Related U.S. Application Data

(63) Continuation of application No. PCT/US99/02566, filed on May 2, 1999.

(60) Provisional application No. 60/073,749, filed on Feb. 5, 1998.

(51) Int. Cl.
- *A61M 5/00* (2006.01)
- *A61M 5/32* (2006.01)
- *A61M 29/00* (2006.01)
- *A61B 1/04* (2006.01)

(52) U.S. Cl. .................. 604/195; 604/110; 604/95.04; 604/198; 604/102; 604/194; 600/115; 600/114

(58) Field of Classification Search ................ 600/114, 600/115, 578, 201, 233; 604/271, 98.02, 604/110, 190, 192–198, 263, 220, 102, 95–98, 604/71, 136, 218, 187, 171; 606/192, 194, 606/133; 138/98, 141; 264/102
See application file for complete search history.

(56) References Cited

U.S. PATENT DOCUMENTS

| | | | | |
|---|---|---|---|---|
| 4,838,869 A | * | 6/1989 | Allard | 604/195 |
| 5,085,640 A | * | 2/1992 | Gibbs | 144/145.1 |
| 5,374,250 A | * | 12/1994 | Dixon | 604/110 |
| 5,484,421 A | | 1/1996 | Smocer | |
| 5,487,734 A | | 1/1996 | Thorne | |
| 5,531,694 A | | 7/1996 | Clemens | |
| 5,964,735 A | * | 10/1999 | Alexander | 604/110 |
| 5,984,898 A | * | 11/1999 | Garvin | 604/195 |
| 6,001,080 A | * | 12/1999 | Kuracina et al. | 604/164.08 |
| 6,015,438 A | * | 1/2000 | Shaw | 604/195 |
| 6,036,674 A | * | 3/2000 | Caizza et al. | 604/195 |
| 6,090,077 A | * | 7/2000 | Shaw | 604/195 |
| 6,123,688 A | * | 9/2000 | Botich et al. | 604/220 |
| 6,179,812 B1 | * | 1/2001 | Botich et al. | 604/110 |

OTHER PUBLICATIONS

Tierney et al, Current Medical & Treatment, 1999, Appleton & Lang, 38th edition, pp. 261-262.*

* cited by examiner

*Primary Examiner*—Brian Casler
*Assistant Examiner*—Roz Maiorino
(74) *Attorney, Agent, or Firm*—Stephen H. Eland; Dann, Dorfman, Herrell and Skillman

(57) ABSTRACT

A method for withdrawing a fluid sample from a patient is disclosed comprising the steps of: a) providing a sampling device (10) having a housing (20) and a needle (40) having a sharpened tip for piercing the skin of the patient; b) withdrawing fluid from the patient into the housing; c) retracting the needle so that the sharpened tip of the needle is enclosed within the housing; and d) expelling the fluid from the housing after the needle is retracted.

20 Claims, 9 Drawing Sheets

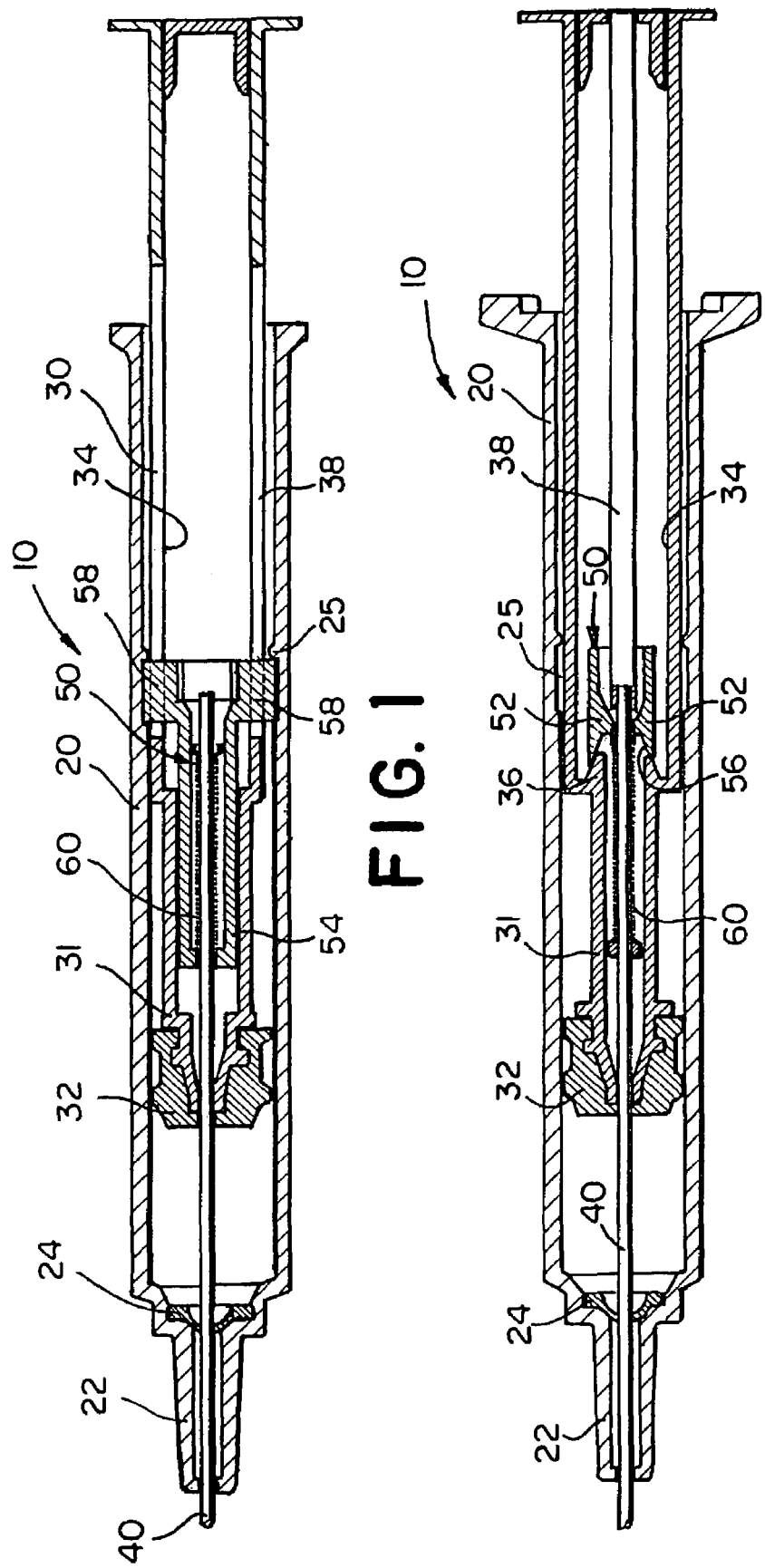

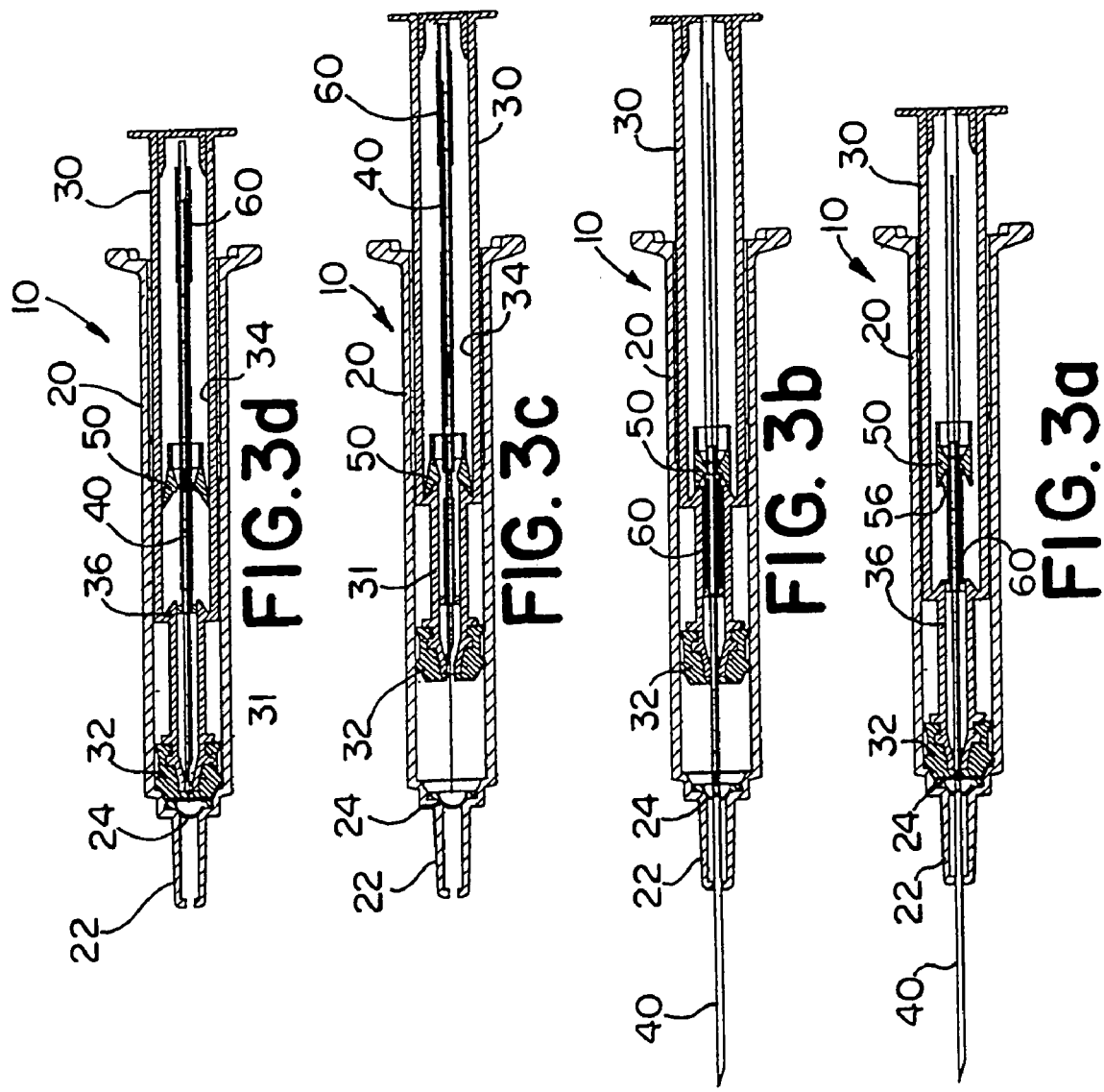

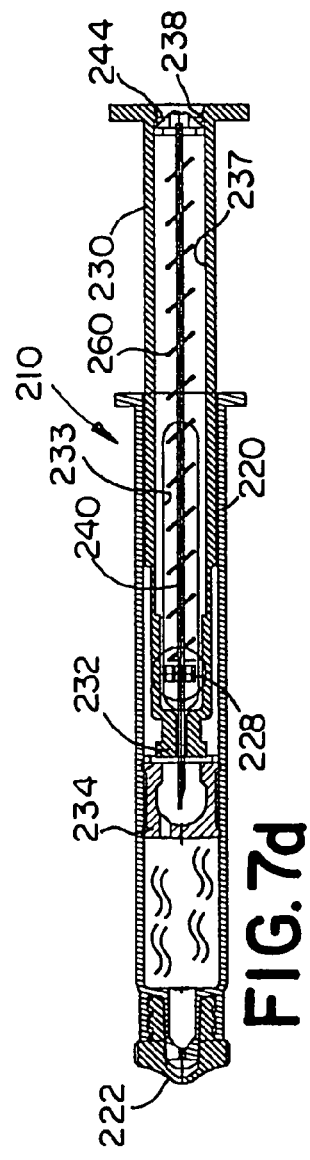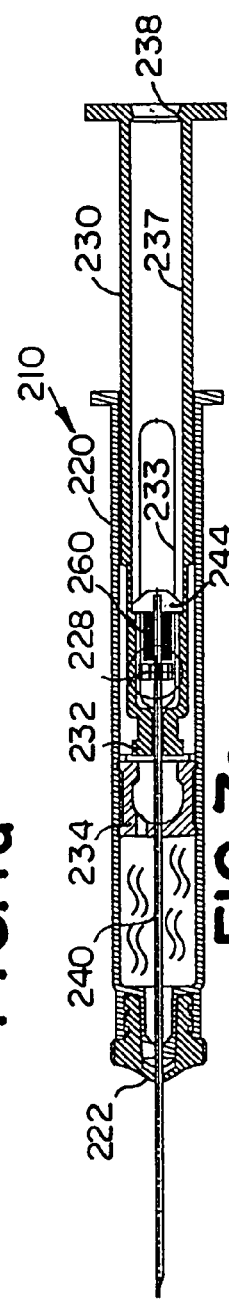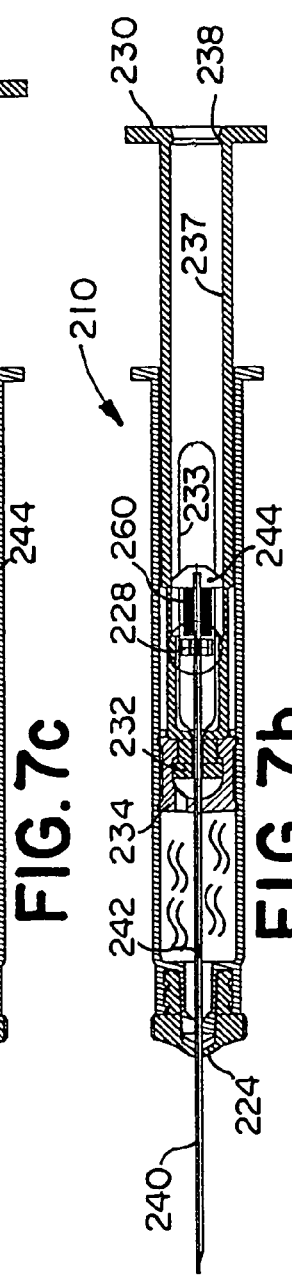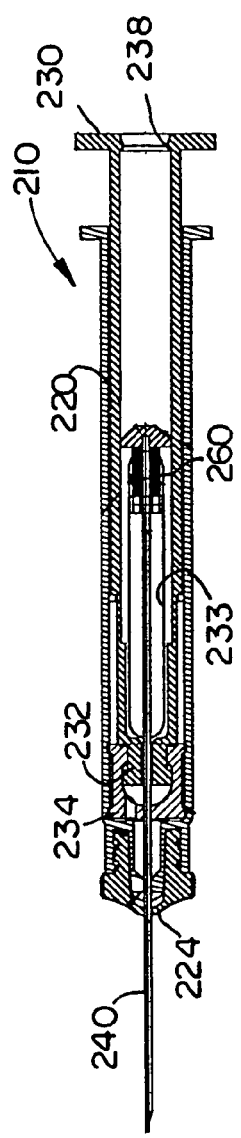

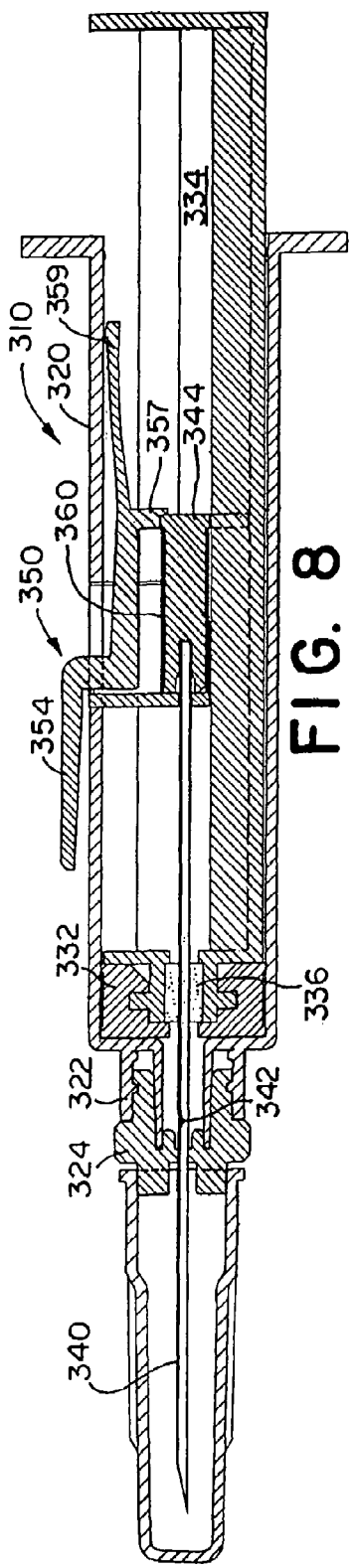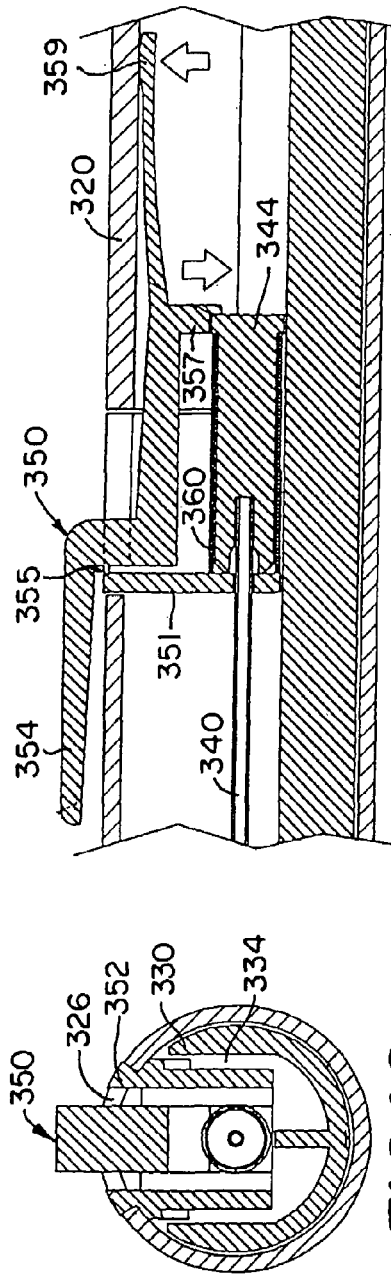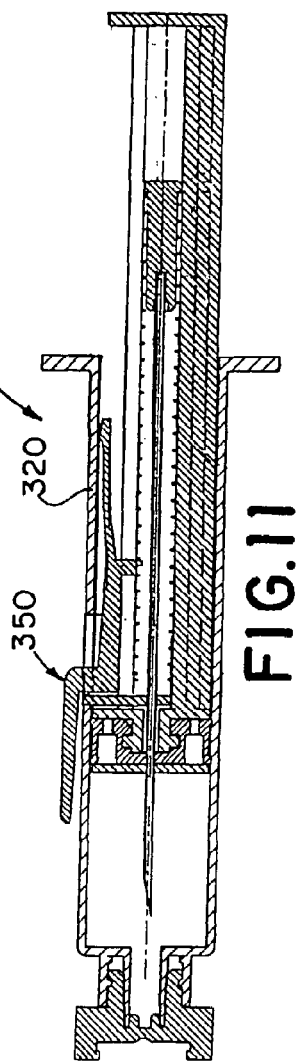

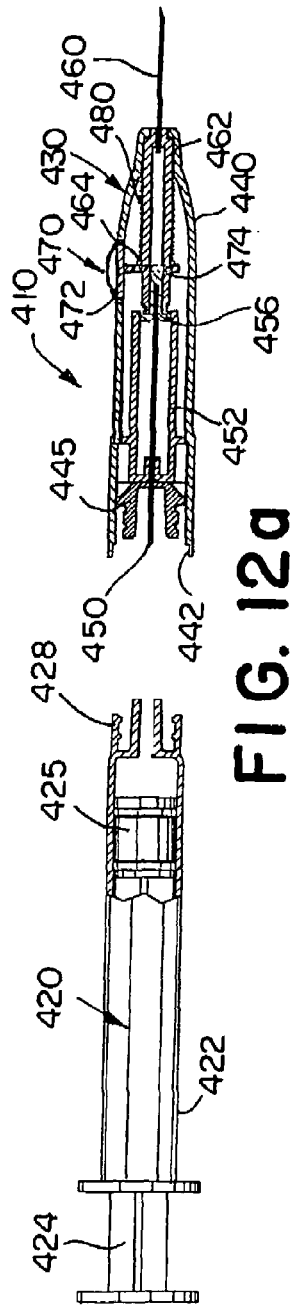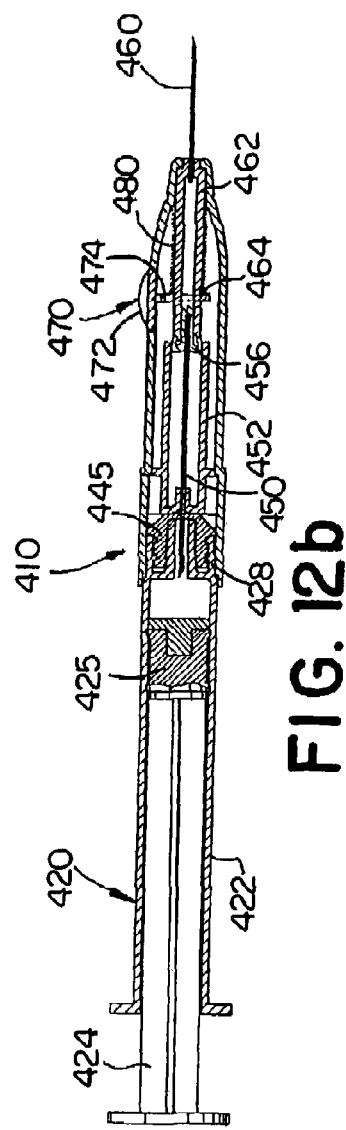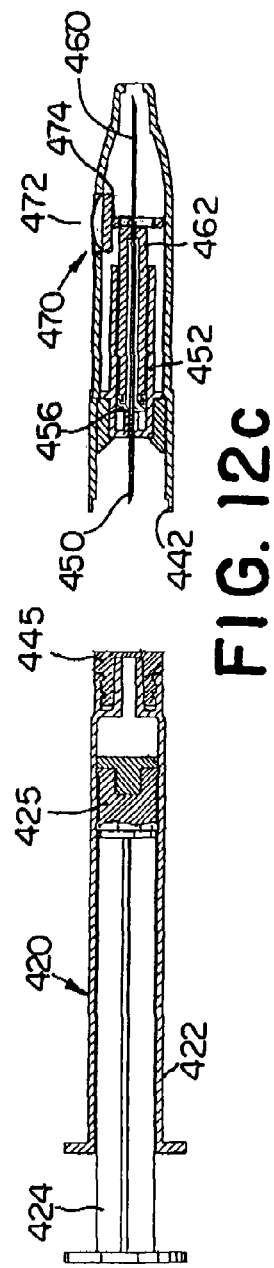

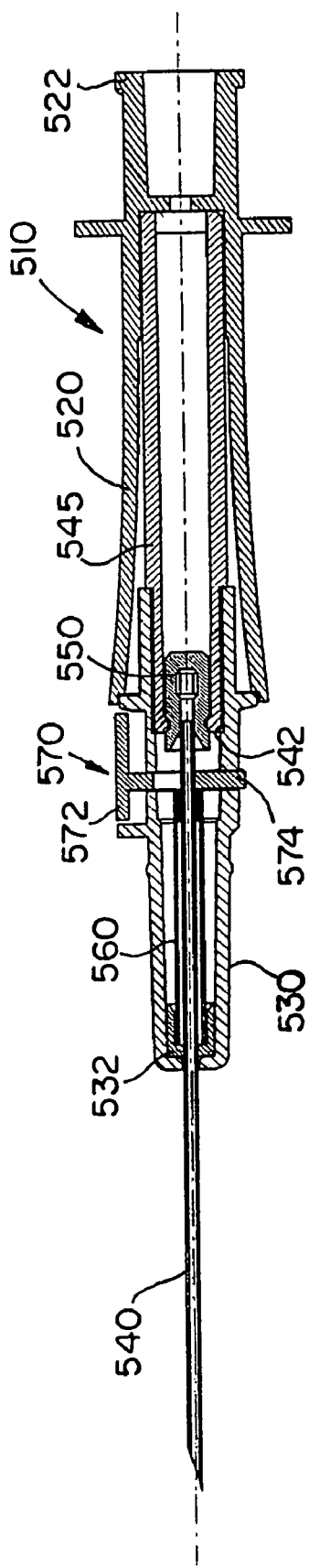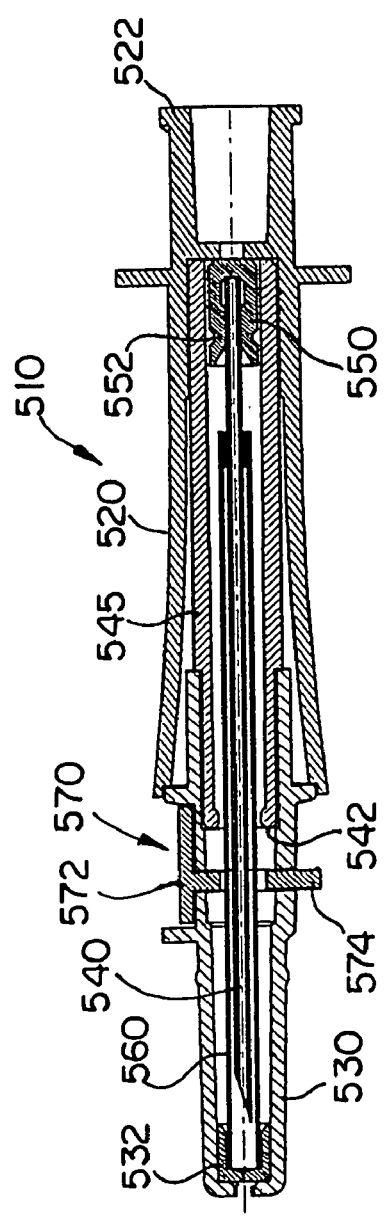

FLUID SAMPLING DEVICE WITH RETRACTABLE NEEDLE

This application is a continuation of International Patent Application No. PCT/US99/02566, filed May 2, 1999, which claims priority to U.S. Provisional Application No. 60/073,749, filed Feb. 5, 1998, which are hereby incorporated herein by reference.

FIELD OF INVENTION

The present device relates to the field of medical devices for fluid sampling. More specifically, the present invention relates to such medical devices having a retractable needle, so that the device is rendered safe after use. In particular, the present invention relates to a device for drawing blood from a patient, wherein after use the needle retracts so that the contaminated needle is enclosed thereby preventing inadvertent contact with the contaminated needle.

BACKGROUND

The present invention relates to a type of medical device that is used to take a sample of arterial blood. An arterial blood collection is done commonly in emergency room settings, as well as hospitals to test for various conditions, such as blood oxygen levels and pH. The standard devices currently used are coated with heparin to prevent blood clotting and the fit between the plunger piston and the barrel is loose enough to allow the arterial blood pressure to move the piston as the device fills with arterial blood. These requirements complicate the reaction of the needle.

SUMMARY OF THE INVENTION

In light of the foregoing, the present invention provides an apparatus and method for collecting fluid samples from a patient. The device comprises a housing, a plunger slidably displaceable within the housing and a needle having a sharpened tip for piercing a patient. The needle is operable to pierce the skin of a patient. Fluid from the patient collects in a fluid chamber within the housing. After the sample is collected, the needle is retracted into the housing so that the sharpened tip is enclosed. After the needle is retracted a pair of seals prevent the sample from leaking from the fluid chamber. In addition, the seals preferably operate to prevent air from entering the fluid chamber after the needle is retracted. The fluid can then be expelled from the fluid chamber by displacing the plunger within the housing.

DESCRIPTION OF THE DRAWINGS

The foregoing summary as well as the following detailed description of the preferred embodiment can be best understood when read in connection with the following drawings in which:

FIG. 1 is a top view of a fluid sampling medical device having a retractable needle;

FIG. 2 is a side view of the fluid sampling medical device shown in FIG. 1;

FIG. 3a is a side view of the device shown in FIG. 1, illustrating the device prior to use;

FIG. 3b is a side view of the device shown in FIG. 3a, illustrating the device after a quantity of fluid has been withdrawn;

FIG. 3c is a side view of the device shown in FIG. 3a, illustrating the device with the needle in a retracted position;

FIG. 3d is a side view of the device shown in FIG. 3a, illustrating the device after the fluid sample has been expelled;

FIG. 7a is a side view of the device shown in FIG. 6, illustrating the device prior to use;

FIG. 7b is a side view of the device shown in FIG. 7a, illustrating the device after a quantity of fluid has been withdrawn;

FIG. 7c is a side view of the device shown in FIG. 7a, illustrating the device with the piston separated from the plunger;

FIG. 7d is a side view of the device shown in FIG. 7a, illustrating the device with the needle in a retracted position;

FIG. 8 is a side view a fourth embodiment of a fluid sampling medical device having a retractable needle;

FIG. 9 is an enlarged fragmentary sectional view of the device shown in FIG. 8;

FIG. 10 is a cross-sectional view of the device shown in FIG. 9, taken along the line 10—10;

FIG. 11 is a side view of the device shown in FIG. 8, illustrating the device with the needle in a retracted position;

FIG. 12a is an exploded side view of a combination syringe and removable needle assembly;

FIG. 12b is a side view of the device shown in FIG. 12a, illustrating the needle assembly attached to the syringe;

FIG. 12c is a side view of the device shown in FIG. 12a, illustrating the needle in a retracted position;

FIG. 13a is a side view of a second embodiment of removable needle assembly; and FIG. 13b is a side view of the needle assembly shown in FIG. 13 a, illustrating the needle in a retracted position.

DETAILED DESCRIPTION OF THE PREFERRED EMBODIMENTS

Figure 4:
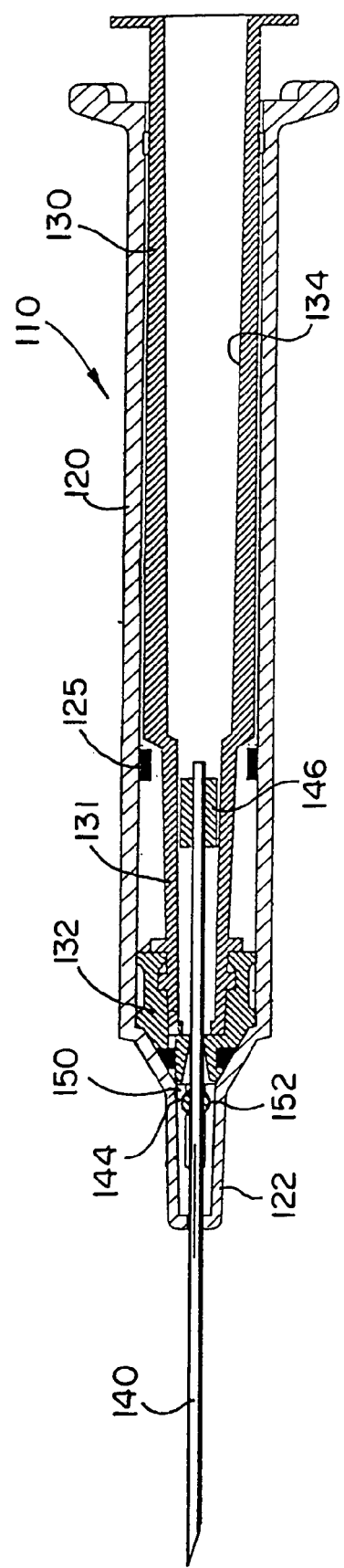
FIG. 4 is a side view of a second embodiment of a fluid sampling medical device having a retractable needle.

Referring now to the drawings and to FIGS. 1–3d specifically, a fluid sampling device is designated generally 10. The device 10 comprises a barrel 20 and a needle 40 projecting forwardly from the forward end of the barrel. A plunger 30 is slidably displaceable within the barrel 20. Fluid is sampled through the needle. For instance, the device may be used to withdraw a quantity of fluid from a patient. The needle 40 pierces the skin of a patient, and blood from the patient flows into the barrel 20. After a sufficient amount of blood has been withdrawn, the needle 40 is retracted into the barrel 20 so that the needle is enclosed, preventing inadvertent contact with the contaminated sharpened point of the needle.

Referring now to FIGS. 1 and 2, the barrel 20 is an elongated generally cylindrical hollow housing. The forward end of the barrel 20 forms a reduced diameter nose piece 22. The nose piece 22 is generally closed, having an aperture for receiving the needle 40.

The plunger 30 has a hollow forward stem 31. An elastomeric piston 32 is attached to the forward end of the plunger stem 31. The piston 32 forms a fluid-tight seal with the interior wall of the barrel 20. The stem is integrally formed with the rearward portion of the plunger, which is an elongated hollow cylindrical portion, which forms a needle chamber 34 for receiving the needle after the needle is retracted. The rearward end of the needle chamber is closed to prevent the needle from being displaced rearwardly of the needle chamber. An actuator 36 is formed at the forward end of the needle chamber 34. The actuator is generally wedge-shpaed and is formed to matingly cooperate with a needle retainer 50 that releasably retains the needle.

The needle 40 includes a side port 42 formed in the side wall of the needle. In addition, the rearward end of the needle is plugged. The needle is disposed so that the side port 42 is located forward of the piston. A variable volume is formed in the barrel between the piston 32 and the forward end of the barrel 20. Accordingly, fluid flowing through the needle is discharged through the side port 42 into the fluid chamber between the piston 32 and the nose 22.

The needle 40 is operable between a projecting position in which the sharpened tip of the needle projects forwardly from the nose 22 of the barrel 20, and a retracted position in which the needle is enclosed within the barrel. A spring 60 circumscribes the needle 40, biasing the needle rearwardly toward the retracted position. The needle retainer 50 releasably retains the needle 40 in the projecting position against the bias of the spring 60. When the actuator 36 engages the needle retainer 50, the needle retainer releases the needle 40, allowing the spring to propel the needle rearwardly into the needle chamber 34.

The needle retainer 50 is rigidly connected to the barrel 20 so that the needle retainer is fixed axially relative to the barrel. The interior wall of the barrel 20 includes a recess that forms a seat 25 for receiving the needle retainer 50. As shown in FIG. 1, the needle retainer 50 comprises a pair of connecting tabs 58 that form a snap fit or friction fit with the seat 25 in the wall of the barrel. The connecting tabs 58 project through a pair of slots 38 in the side walls of the plunger 30. The slots allow the plunger to be displaced axially relative to the needle retainer.

The needle retainer 50 includes at least one finger or latch 52 for releasably retaining the needle. In the present instance, the fingers 52 are bonded to the needle by UV curable epoxy. Alternatively, a block can be attached to the needle and the finger can abut the block to retain the needle against rearward axial displacement.

The forward end of the fingers form a tapered actuation surface 56 that cooperates with the tapered actuator 36 on the plunger. When the plunger is displaced rearwardly, the actuator 36 engages the tapered actuation surface 56 of the needle retainer, wedging the fingers apart. In this way, the fingers are displaced radially outwardly out of engagement with the needle. The spring then propels the needle rearwardly into the needle chamber 34.

The needle retainer 50 further includes a spring housing 54 projecting forwardly from the fingers 52. The forward end of the spring housing 54 form a bearing surface against which the forward end of the spring 60 bears. The rearward end of the spring is bonded to the needle. Alternatively, if a block is attached to the needle, the rearward end of the spring may bear against the block.

As shown in FIGS. 1 and 2, in the projecting position, the forward end of the needle projects from the forward end of the barrel 20. The needle also projects through the piston 32 and into the needle retainer 50. The piston 32 includes a pierceable septum that forms a fluid-tight seal with the exterior surface of the needle to prevent fluid from leaking from the barrel into the plunger 30. In addition, in the projecting position, the needle pierces a nose seal 24 disposed within the nose 22 of the barrel. The nose seal forms a fluid-tight seal with the exterior surface of the needle to prevent fluid from leaking from the barrel through the nose 22.

The device can be designed to operate in two different manners. In the first manner, the plunger is withdrawn to form a fluid chamber of a particular volume. The needle is then inserted into a patient and blood flows through the needle and into the barrel, filling the fluid chamber. When designed to be used in this manner, a hydrophobic vent is included to prevent the device from becoming airlocked, which would impede the flow of blood into the fluid chamber. The vent is air permeable, but is not permeable to blood The vent allows air from the fluid chamber to be discharged from the fluid chamber as the blood enters the fluid chamber, but prevents blood from leaking from the fluid chamber.

Alternatively, the device 10 can be configured to operate so that the blood pressure displaces the plunger rearwardly as blood enters the fluid chamber. During such use, the plunger is displaced forwardly so that the piston is disposed at the forward end of the barrel, engaging the forward wall of the barrel. The needle is then inserted into the patient and blood flows into the barrel, displacing the piston 32 rearwardly as blood enters the barrel. When designed to be used in such a manner, the device does not need a vent for venting air from the fluid chamber. In addition, the piston or the barrel wall is lubricated to reduce the friction between the piston and the barrel to facilitate displacing the plunger.

Referring now to FIGS. 3a–3d, the device operates as follows. In FIG. 3a, the device is shown prior to use. The needle 40 is inserted into a patient's blood vessel, and blood flows into the fluid chamber in the barrel as shown in FIG. 3b. Referring to FIG. 3c, the plunger is then displaced axially rearwardly so that the actuator 36 engages the needle retainer 50 displacing the fingers 52 radially outwardly to release the needle. The spring 60 then propels the needle rearwardly into the needle chamber so that the needle is enclosed with in the barrel. After the needle retracts, the septum of the piston that was pierced by the needle reseals to prevent blood from leaking into the plunger. In addition, the nose seal 24 reseals to prevent blood from leaking through the nose 22. In this way, the sample is sealed within the fluid chamber against contact with the air. Referring now to FIG. 3d, after the needle is retracted, the sample can discharged from the syringe so that the sample can be tested. The sample is discharged by displacing the plunger forwardly. Displacing the piston forwardly creates sufficient fluid pressure to expel the fluid through the hole in the nose seal membrane that was formed by the needle.

Figure 5:
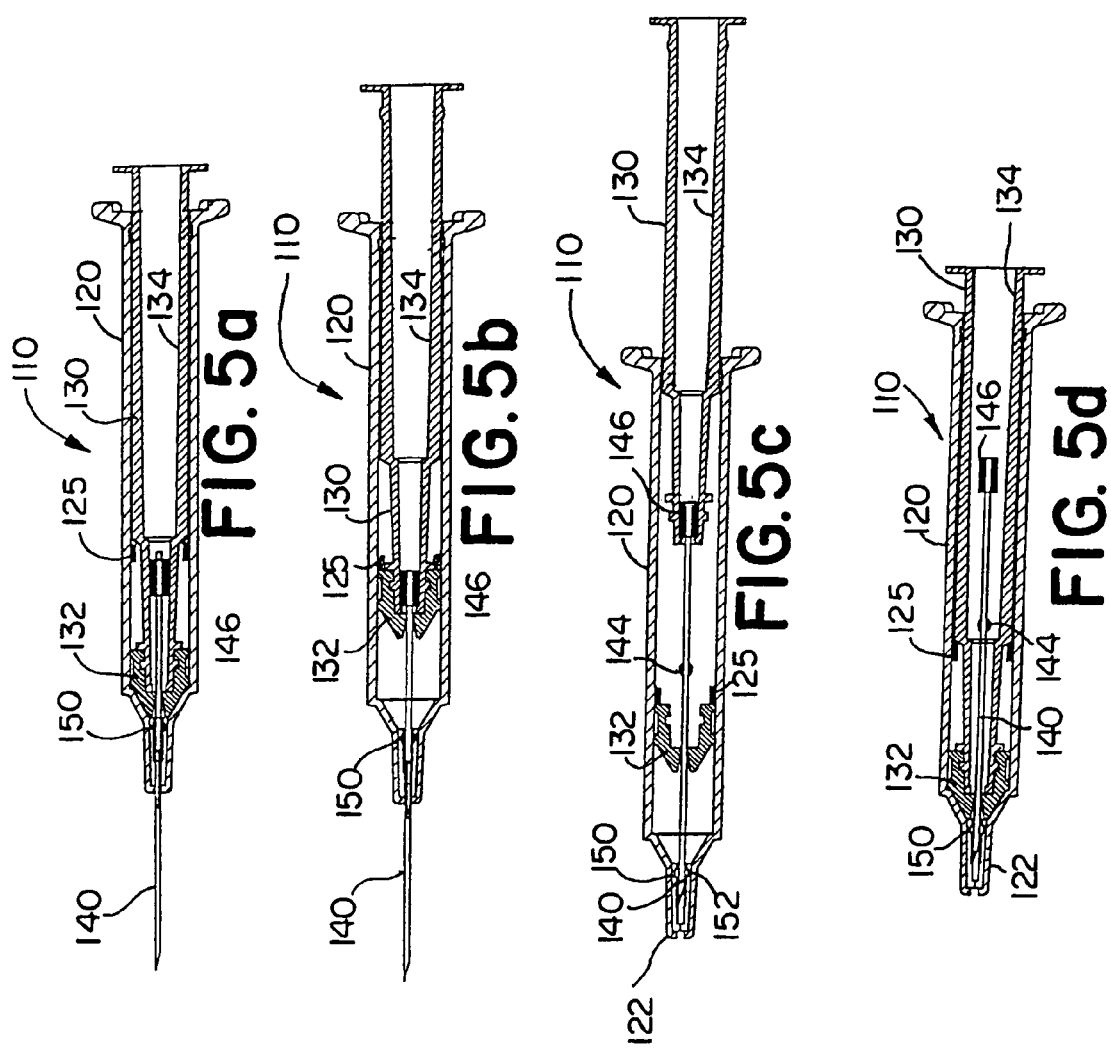
FIG. 5a is a side view of the device shown in FIG. 4, illustrating the device prior to use.
FIG. 5b is a side view of the device shown in FIG. 5a, illustrating the device after a quantity of fluid has been withdrawn.
FIG. 5c is a side view of the device shown in FIG. 5a, illustrating the device with the needle in a retracted position.
FIG. 5d is a side view of the device shown in FIG. 5a, illustrating the device after the fluid sample has been expelled.

Referring now to FIGS. 4–5d, a second embodiment 110 of a fluid sampling device is shown. The device 110 includes a barrel 120 and a retractable needle 140 projecting forwardly from the barrel. A plunger 130 is slidably displaceable within the barrel. After a fluid sample is collected in the device, the needle is retracted into the barrel so that the needle is enclosed to prevent inadvertent contact with the contaminated needle. After the needle is retracted, the fluid is sealed within a fluid chamber in the barrel. The fluid sample can then be discharged so that the sample can be tested.

The plunger 130 includes a tapered hollow stem 132. An elastomeric piston 132 is removably attached to the forward end of the stem. The piston forms a fluid-tight seal with the interior of the barrel. Preferably, a hydrophobic plug 136 extends through the piston, providing a vent for gases in the fluid chamber between the piston and the forward end of the barrel. An inwardly projecting annular flange or stop ring 125 limits the rearward axial displacement of the piston. After the piston engages the ring stop 125, continued rearward displacement of the plunger detaches the piston from the plunger.

The plunger stem projects forwardly from the rearward portion of the plunger, which is an elongated generally cylindrical hollow portion, forming a needle chamber 134. The stem 132 is also hollow, forming a forward chamber 137 for receiving the rearward end of the needle when the needle 140 is disposed in the retracted position. The forward end of the forward chamber is smaller in diameter than a block 146 attached to the rearward end of the needle. In this way, upon rearward displacement of the plunger, the interior wall of the forward chamber 137 engages the block 146 on the needle urging the needle rearward. This in turn displaces the needle out of engagement with a needle retainer 150 so that continued rearward displacement of the plunger retracts the needle rearwardly.

The forward end of the barrel 120 forms a reduced diameter nose 122. The needle projects forwardly from the nose 122 in the projecting position. In this position, the needle passes through an opening in the forward end of the piston. The forward opening in the piston is smaller in diameter than the needle, so that the piston forms a fluid-tight seal around the exterior of the needle.

A needle retainer 150 releasably retains the needle in the projecting position. In the present instance, the needle retainer comprises a pair of receptacles 152 that cooperate with and engage a spherical detent 144 fixed to the needle.

The device 120 operates as follows. Referring to FIG. 5a, the device 110 is shown prior to use. The plunger 130 is displaced rearwardly to provide a fluid chamber for receiving the fluid sample. The needle is then inserted into the artery of the patient. Blood flows through the needle into the fluid chamber through a side port in the needle to collect the sample, as shown in FIG. 5b. Referring to FIG. 5c, after the sample is collected, the plunger is displaced rearwardly to detach the piston from the plunger. The plunger is further displaced rearwardly to retract the needle into the barrel. Referring to FIG. 5d, the sample can then be expelled by driving the plunger forward to re-engage the piston and then drive the piston forwardly.

Figure 6:
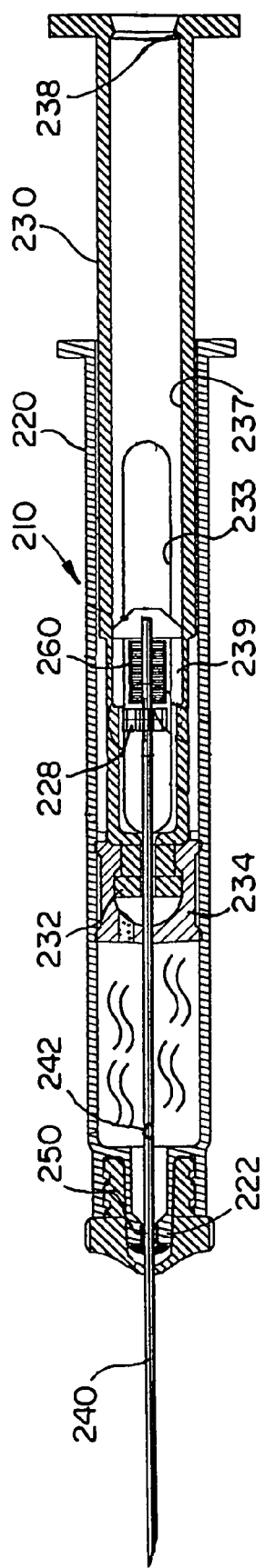
FIG. 6 is a side view of third embodiment of a fluid sampling medical device having a retractable needle.

Referring now to FIGS. 6–7d, a third embodiment of a fluid sampling medical device 210 is illustrated. The device includes a barrel 220 and a retractable needle 240 projecting from the forward end of the barrel. A plunger 230 is slidably displaceable within the barrel. After a fluid sample is collected from the patient, the needle retracts into the barrel to enclose the contaminated needle.

The barrel is generally cylindrical and hollow. The plunger 230 includes an elastomeric piston 234 that forms a fluid-tight seal with the interior wall of the barrel. The plunger 230 is hollow, having a forward chamber 239 housing the spring before the needle is retracted, and a rearward needle chamber 237 for receiving the needle after the needle is retracted.

A spring 260 circumscribing the needle biases the needle rearwardly towards the retracted position. The spring is disposed about the needle 240 between a fixed spring block 228 and a needle block 244 connected to the rearward end of the needle. The spring block 228 is fixedly attached to the barrel 220. Accordingly, slots 233 are formed in the side of the plunger 230 to provide clearance for the spring block 228 when the plunger is displaced within the barrel.

A needle retainer 250 releasably retains the needle in the projecting position against the bias of the spring 260. In the present instance, the needle retainer is epoxy that bonds the needle to the nose 222.

Referring to FIGS. 7a–7d, the device operates as follows. In FIG. 7a, the device is illustrated prior to use. The plunger 230 is withdrawn to provide a fluid chamber between the piston 234 and a resealable seal 224 that is disposed in the nose of the barrel and provides a fluid-tight seal with the exterior of the needle 240. Referring to FIG. 7b, the needle 240 is inserted into a patient's artery, and blood flows through a side port 242 in the needle 240 and into the fluid chamber. Once the sample is collected the needle is withdrawn from the patient. Referring to FIG. 7c, the plunger 230 is then displaced rearwardly. The rearward displacement brings the piston 234 into engagement with an annular flange projecting inwardly from the interior wall of the barrel. Continued rearward displacement of the plunger detaches the piston 234 from the stem 232 of the plunger. In addition, the rearward displacement brings an annular flange 238 into engagement with the needle block 244. Referring to FIG. 7d, further rearward displacement of the plunger breaks the bond between the nose 222 and the needle, releasing the needle from the needle retainer 250. The spring then propels the needle rearwardly into the needle chamber. The nose seal 224 reseals to prevent the sample from leaking through the nose 222 of the barrel. In addition, the forward end of the piston 234 reseals to prevent the sample from leaking into the plunger. In this way, the nose seal 224 and the piston 234 seal the sample within the fluid chamber to prevent the sample from contacting the air. After the needle is retracted, the sample can be expelled from the barrel into equipment for testing the sample by driving the plunger forwardly.

Referring now to FIGS. 8–11, a fourth embodiment of a fluid sampling device 310 is shown. The device includes a barrel 320, a retractable needle 340 and a plunger 330 slidably displaceable within the barrel. This third embodiment allows the operator to actuate retraction of the needle regardless of the axial position of the plunger.

The barrel 320 is generally cylindrical. The forward end of the barrel is generally closed, forming a reduced diameter opening. A female Luer-type fitting 322 projects from the forward end of the barrel 320. An elastomeric seal threadedly engages the Luer fitting 322. The seal 324 includes a pierceable membrane through which the needle 340 projects. The membrane forms a fluid-tight seal with the exterior of the needle 340.

The plunger 330 includes a piston 332 that forms a fluid-tight seal with the interior wall of the barrel. In addition, the piston 332 includes a pierceable membrane through which the needle projects. The piston membrane forms a fluid-tight seal with the exterior of the needle. In addition, the piston includes a hydrophobic plug 336 that allows gas to vent from the fluid chamber between the piston and the nose seal 324. Referring to FIGS. 10 and 11, the plunger 330 is a generally U-shaped channel, having a needle chamber 334 for receiving the retracted needle 340. A longitudinal, axially elongated rib 335 projects upwardly into the needle chamber 334.

Referring now to FIGS. 8–10, a manually operable needle retainer 350 releasably retains the needle in the projecting position against the bias of the spring 360 biasing the needle rearwardly toward the retracted position. The needle retainer 350 comprises an actuating lever 354 and a latch that engages a block 344 attached to the needle. As shown in FIG. 9, the latch 354 engages the needle block 344 to releasably retain the needle. By operating the actuator lever 352, the latch 357 pivots radially outwardly out of engagement with the needle block 344. The spring 360 then propels the needle rearwardly toward the retracted position.

The latch 357 is biased into engagement with the needle block 344. In the present instance, a spring finger 359 biases the latch into engagement with the needle block. The spring finger 359 is integral with the latch and projects rearwardly from the latch. The spring finger 359 resiliently flexes and engages the interior wall of the barrel 320. When the actuating lever 354 is operated, the latch displaces radially outwardly, thereby resiliently deforming the spring finger 359.

Referring to FIG. 10, the needle retainer 350 is attached to the barrel 320 by mounting brackets 352. The mounting brackets 352 engage a slot 326 formed in the top of the barrel. The mounting brackets 352 fix the needle retainer relative to the plunger 330. A transverse spring block 351 is connected to the needle retainer assembly. The spring block forms a forward bearing surface for the spring 360. The actuating lever 354 is attached to the spring block 351 by a flexible web or living hinge 355. The web 355 forms a pivot point for the actuating lever 354.

The device operates as follows. The plunger 330 is withdrawn to provide a fluid chamber for receiving a blood sample from a patient. The needle 340 is inserted into a patient's artery. Blood flow through a side port 342 in the needle and into the fluid chamber. Once a sufficient amount of blood is withdrawn, the needle is withdrawn from the patient. The actuating lever is depressed to pivot the latch 357 thereby releasing the needle from the needle retainer 350. The spring 360 then propels the needle rearwardly into the needle chamber. After the needle is retracted, the nose seal 324 reseals to prevent from blood from leaking from the fluid chamber. The fluid sample can then be expelled from the device into separate device to test the sample. The sample is expelled by driving the plunger forwardly within the barrel.

Referring now to FIGS. 12a–12c, a device for collecting a fluid sample such as blood is designated generally 410. The device 410 comprises a syringe 420 and a removably connectable needle assembly 430. The needle assembly 430 comprises a retractable insertion needle 460 for piercing a patient's skin. When the needle assembly 430 is connected to the syringe 420, the insertion needle 460 is in fluid communication with the interior of the syringe. After the fluid sample is collected in the syringe 420, the insertion needle 460 can be retracted into the housing of the needle assembly 430 to prevent inadvertent contact with the contaminated insertion needle. The needle assembly 430 can also be removed from the syringe 420 after the fluid sample is collected. The fluid sample can then be transferred to where the sample is to be tested. The sample can then be expelled from the syringe 420 and tested.

The syringe 420 is similar to a typical syringe, having a barrel 422, a plunger 424 with a piston 425 slidably displaceable within the barrel and a Luer-type fitting 428 on the nose of the barrel. The piston 425 forms a fluid-tight seal with the interior wall of the barrel 422, and driving the plunger forward expels fluid from the syringe 420.

The needle assembly 430 is adapted to connect to the Luer fitting 428 of the syringe so that the needle assembly can be utilized with standard syringes that are already in widespread use throughout the medical field. Accordingly, the housing 440 of the needle assembly 430 includes an opening at the rearward end, forming a socket 442 for engaging the Luer fitting 428 of the syringe. A seal 445 having a pierceable resealable membrane is disposed within the socket 442. The seal 445 is externally threaded having threads that cooperate with the Luer fitting 428.

The needle assembly 430 comprises two needles a forward insertion needle 460 that projects forwardly from the front end of the housing 440, and a fixed needle 450 disposed within the housing 440. The fixed needle 450 projects into the socket 442, piercing the Luer seal 445. The fixed needle 450 is attached to a fixed needle tube 452 that is fixedly attached to the housing 440. The rearward end of the fixed needle tube is generally closed, having a reduced diameter through which the fixed needle 450 projects. The fixed needle is fixedly connected to the fixed needle tube 452 to form a fluid-tight connection between the exterior surface of the fixed needle and the generally closed rearward end of the fixed needle tube.

The insertion needle 460 is fixedly connected to a telescoping needle tube 462 that telescopingly engages the interior of the fixed needle tube 452. A needle seal 456 disposed within the forward end of the fixed needle tube 452 provides a fluid-tight seal between the fixed needle tube and the telescoping needle tube. The insertion needle projects forwardly from the forward end of the telescoping needle tube 462. An annular flange 464 projects outwardly from the telescoping needle tube 462. A spring 480 circumscribing the telescoping needle tube 462 is disposed between the flange 464 and the interior of the forward end of the housing. The spring 480 bears against the flange 464 biasing the telescoping needle tube 462 and the attached insertion needle 460 rearwardly.

A needle retainer 470 releasably retains the insertion needle 460 against the bias of the spring 480. The needle retainer 470 comprises an actuator button 472 and a latch 474. The latch 474 has an aperture through which the telescoping needle tube 462 projects. In the latched position, the latch 474 is disposed so that the rim of the aperture engages the flange 464 to retain the telescoping needle tube against the bias of the spring. Depressing the actuator button 472 displaces the latch 474 downwardly so that the latch aperture is aligned with the annular flange 464. The spring 480 then propels the telescoping needle tube rearwardly into the fixed needle tube, so that the insertion needle is enclosed within the housing 440.

Accordingly, the device 410 operates as follows. The plunger 424 is disposed so that the piston 425 is located at the forward end of the syringe barrel 422. The needle assembly 430 is connected to the front end of the syringe 420. The rear fixed needle 450 projects through the Luer seal 445 and into the barrel. The insertion needle 460 is then inserted into a patient's artery and blood flows from the patient into the interior of the syringe. The pressure of the blood flow drives the piston and plunger 424 rearwardly as the blood enters the syringe 420. After a sufficient amount of blood is collected, the insertion needle is withdrawn from the patient. The actuator button 472 is depressed to actuate retraction of the insertion needle. The insertion needle then retracts into the housing. The needle assembly 430 is then detached from the syringe 420. The Luer seal 445 remains on the Luer-fitting 428 of the syringe, sealing the forward end of the syringe to prevent fluid from leaking out of the nose of the syringe 420. The piston 425 forms a fluid-tight seal with the barrel to prevent fluid from leaking out of the rearward end of the syringe. The sealed fluid sample can then be transported to an area for testing the sample and then expelled from the syringe by driving the plunger forwardly within the barrel.

Referring now to FIGS. 13a and 13b a second embodiment of a needle assembly that is operable in connection with a syringe is designated generally 510. The needle assembly includes a housing 520 and a retractable needle 540 projecting forwardly from the housing. The rearward end of the housing forms a socket 522 for connecting the needle assembly to a syringe similar to the manner described above in connection with the device designated 410 and illustrated in FIGS. 12a–12c. However, in the present instance, the socket 522 is configured as a female tapered Luer-type fitting to cooperate with a male Luer-type fitting on a syringe.

The needle assembly 510 includes a generally cylindrical nose piece 530 attached to the forward end of the housing 520. A nose seal 532 forms a fluid-tight seal with the exterior of the needle 540. A generally cylindrical needle tube 545 is disposed within the housing 520 and projects into the rearward end of the nose piece 545. The forward end wall of the socket 522 has a reduced diameter opening so that the needle tube 545 is in fluid communication with the socket. An annular detent 542 projects inwardly into the needle tube adjacent the forward end of the needle tube 545. An elastomeric valve 550 seals the forward end of the needle tube 545. The valve 550 has an external circumferential groove 552. The annular detent 542 engages the circumferential groove to releasably retain the valve 550.

The rearward end of the needle 540 projects into the valve 550. The forward end of the needle 540 projects forwardly from the nose piece. A spring 560 attached to the needle biases the spring rearwardly to a retracted position within the housing 520. A needle retainer 570 releasably retains the needle in the projecting position against the bias of the spring.

The needle retainer 570 is configured similarly to the needle retainer described above in connection with the previous device 410. The retainer 570 comprises a button actuator 572 and a latch 574. The latch has an aperture. In the latched position, the rim of the latch aperture engages the end of the spring 560. When the actuator button 572 is depressed, the latch is displaced downwardly, aligning the latch aperture with the spring, thereby allowing the spring to propel the needle rearwardly as shown in FIG. 13b.

Accordingly, the device operates as follows. The needle assembly 510 is attached to a syringe. The needle is then inserted into a patient's artery. Blood flows through the needle 540, and through the valve 550 into the needle tube 545. From the needle tube the blood flows into the syringe, where the sample collects. After a sufficient amount of blood is removed, the needle 540 is removed from the patient. The actuator button 572 is depressed to release the needle 540. The spring 560 propels the needle rearwardly. The needle is driven further within the valve, sealing the rearward end of the needle. In addition, the spring biases the valve against the opening into the socket to seal the socket opening. The needle assembly thereby operates as a seal, sealing the forward end of the syringe. The needle assembly can be detached if desired. The syringe can then be sealed with a cap and transported to an area where the sample is to be tested. The sample can then be expelled from the syringe by driving the plunger forward.

While particular embodiments of the invention have been illustrated and described above, it is not intended to limit the invention to such disclosure. It will be recognized that changes and modifications may be made within the scope of the following claims.

We claim:

1. A method for withdrawing a fluid sample from a patient, comprising the steps of:
   a. providing a sampling device having a housing, a plunger and a needle having a sharpened tip for piercing the patient
   b. collecting fluid from the patient in the housing;
   c. retracting the needle into the plunger so that the sharpened tip of the needle is enclosed within the plunger to prevent inadvertent contact with the sharpened tip; and
   d. expelling the fluid from the housing after the sharpened tip of the needle is retracted into the plunger.

2. The method of claim 1 wherein the step of expelling fluid comprises the step of displacing the plunger within the housing.

3. The method of claim 1 comprising the step of sealing the fluid within the housing.

4. The method of claim 1 wherein the step of retracting comprises the step of displacing the needle rearwardly into the housing while the collected fluid is in the housing.

5. The method of claim 1 comprising the step of analyzing the collected fluid to determine a characteristic of the collected fluid.

6. The method of claim 5 comprising the step of analyzing the pH level of the collected fluid.

7. The method of claim 5 comprising the step of analyzing the oxygen levels of the collected fluid.

8. The method of claim 1 comprising the steps of biasing the needle rearwardly and releasably retaining the needle against the rearward bias.

9. The method of claim 8 comprising the step of releasing the needle after the step of collecting fluid so that the needle is automatically retracted rearwardly by the biasing element.

10. The method of claim 9 wherein the method comprises the step of displacing the plunger rearwardly, and the step of releasing the needle occurs in response to displacing the plunger rearwardly.

11. The method of claim 9 wherein the device includes an actuator wherein the step of releasing the needle comprises manually operating the actuator.

12. The method of claim 1 comprising the step of maintaining the needle in a fixed axial position relative to the housing while a majority of the fluid is collected in the housing.

13. The method of claim 1 wherein the housing comprises a reservoir and the step of collecting fluid comprises collecting fluid in the reservoir and the step of expelling comprises expelling the fluid from the reservoir in the housing.

14. The method of claim 1 wherein the housing comprises a port and the step of collecting comprises collecting fluid through the port and the step of expelling comprises expelling the fluid through the port.

15. The method of claim 1 comprising the step of venting air from the housing during the step of collecting fluid.

16. The method of claim 1 wherein the device includes a needle assembly comprising the needle and a hub having a first connector, and the housing comprises a second connector cooperable with the first connector, and the method comprises the step of connecting the first connector to the second connector.

17. The method of claim 16 comprising the step of removing the hub from the barrel prior to the step of expelling fluid from the housing.

18. The method of claim 1 wherein the plunger comprises a piston and the method comprises the step of removing the piston from the plunger.

19. The method of claim 1 wherein the step of expelling comprises expelling the fluid while the needle is retracted in the housing.

20. The method of claim 1 wherein the step of collecting fluid comprises displacing the plunger rearwardly by the fluid pressure of the fluid being collected.

* * * * *